(12) United States Patent
Kim et al.

(10) Patent No.: US 9,850,470 B2
(45) Date of Patent: Dec. 26, 2017

(54) **POLYENE-SPECIFIC GLYCOSYLTRANSFERASE DERIVED FROM *PSEUDONOCARDIA AUTOTROPHICA***

(71) Applicant: INHA-INDUSTRY PARTNERSHIP INSTITUTE, Incheon, KS (US)

(72) Inventors: Eung Soo Kim, Seoul (KR); Mi Jin Lee, Incheon (KR); Hye Jin Kim, Incheon (KR)

(73) Assignee: INHA-INDUSTRY PARTNERSHIP INSTITUTE, Incheon (KR)

( * ) Notice: Subject to any disclaimer, the term of this patent is extended or adjusted under 35 U.S.C. 154(b) by 0 days.

(21) Appl. No.: 14/912,604

(22) PCT Filed: Oct. 28, 2014

(86) PCT No.: PCT/KR2014/010161
§ 371 (c)(1),
(2) Date: Feb. 18, 2016

(87) PCT Pub. No.: WO2015/064998
PCT Pub. Date: May 7, 2015

(65) Prior Publication Data
US 2016/0201038 A1    Jul. 14, 2016

(30) Foreign Application Priority Data
Oct. 30, 2013 (KR) .................. 10-2013-0130264

(51) Int. Cl.
| | | |
|---|---|---|
| *C12N 9/10* | (2006.01) | |
| *C12N 15/00* | (2006.01) | |
| *C12N 1/20* | (2006.01) | |
| *C12P 21/06* | (2006.01) | |
| *C12P 21/04* | (2006.01) | |
| *C07H 21/04* | (2006.01) | |
| *C12N 15/09* | (2006.01) | |

(52) U.S. Cl.
CPC ............ *C12N 9/10* (2013.01); *C12N 9/1048* (2013.01); *C12N 15/09* (2013.01); *C12Y 204/00* (2013.01)

(58) Field of Classification Search
None
See application file for complete search history.

(56) References Cited

U.S. PATENT DOCUMENTS 7,595,156 B2 * 9/2009 Lee .................. C07H 21/04
435/193
2014/0371436 A1   12/2014 Kim et al.

FOREIGN PATENT DOCUMENTS

| KR | 10-2010-0089370 A | 8/2010 |
| WO | 2013-100315 A1 | 7/2013 |

OTHER PUBLICATIONS

Branden et al. Introduction to Protein Structure, Garland Publishing Inc., New York, p. 247, 1991.*
International Search Report for PCT/KR2014/010161 dated Feb. 25, 2015 from Korean Intellectual Property Office.
Kim, Yong-Geong et al., "Investigation of the NPP-specific polyene glycosyltransferase from Pseudonocardia autotrophica", In: KSBE, 2013 Fall Conference and International Symposium, Oct. 16-18, 2013, BEXCO, p. 218, (P0046).
Lee, Mi-Jin et al., "Structural analysis and biosynthetic engineering of a solubility-improved and less-hemolytic nystatin-like polyene in Pseudonocardia autotrophica", Applied Microbiology and Biotechnology, Mar. 1, 2012, vol. 95, No. 1, pp. 157-168.
NCBI, GenBank assession No. AGM12656.1 (May 27, 2013).

* cited by examiner

*Primary Examiner* — Yong Pak
(74) *Attorney, Agent, or Firm* — Revolution IP, PLLC

(57) ABSTRACT

Disclosed is a novel polyene-specific glycosyltransferase derived from *Pseudonocardia autotrophica*. The glycosyltransferase includes an amino acid sequence of SEQ ID NO: 1 and a gene encoding the glycosyltransferase. The glycosyltransferase is produced by a method which includes the steps of: culturing transgenic recombinant microorganisms; and isolating glycosyltransferase from the cultured recombinant microorganisms.

3 Claims, 5 Drawing Sheets

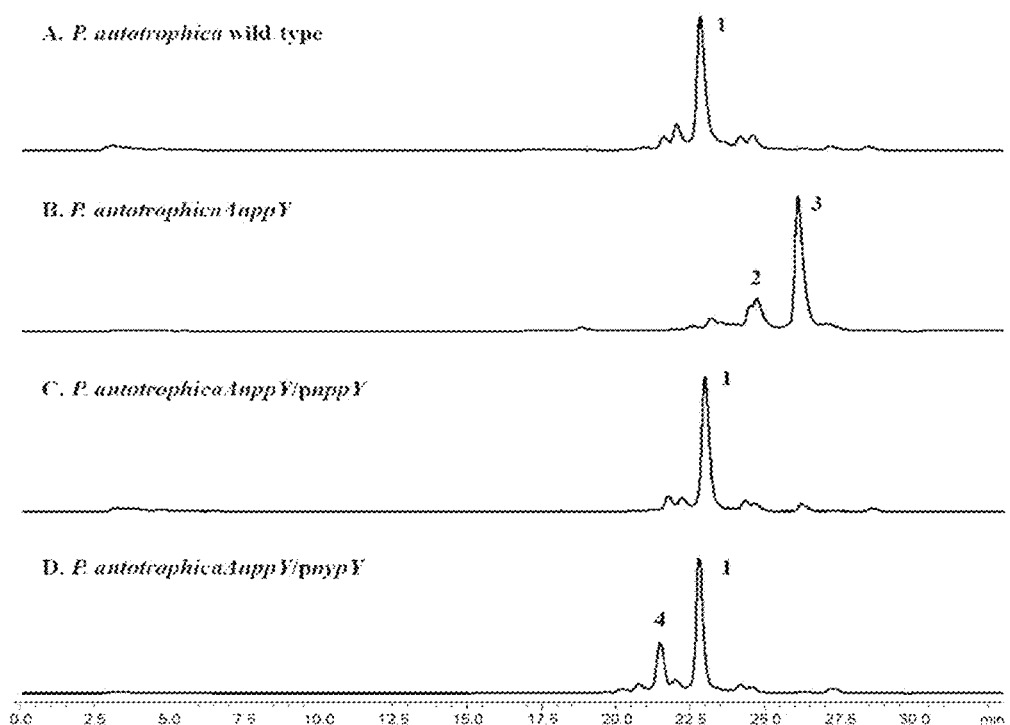

FIG. 4
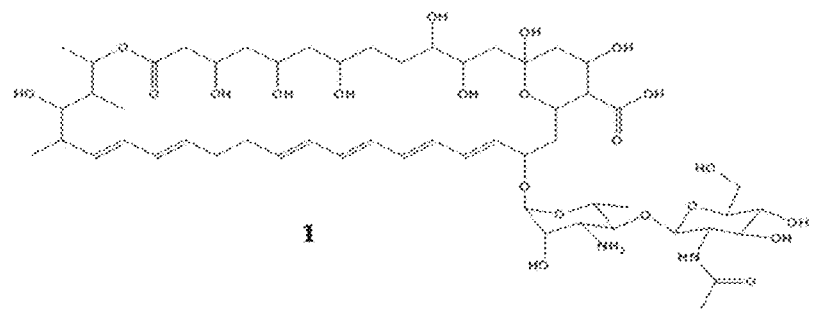
1
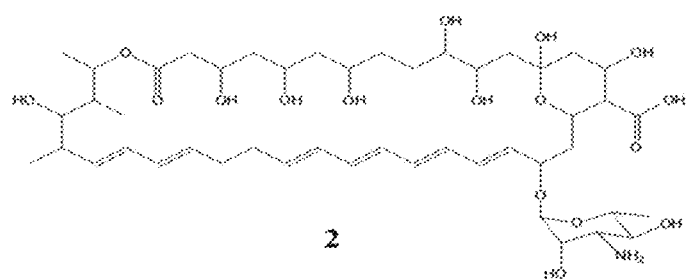
2
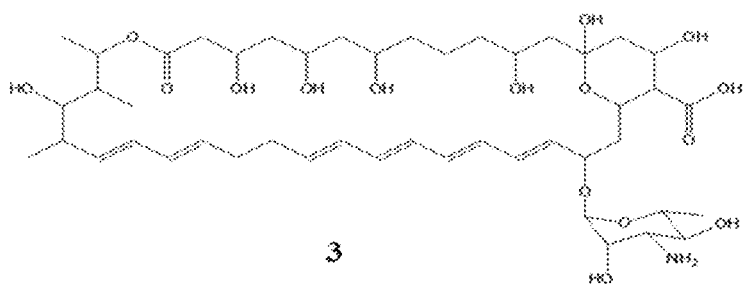
3
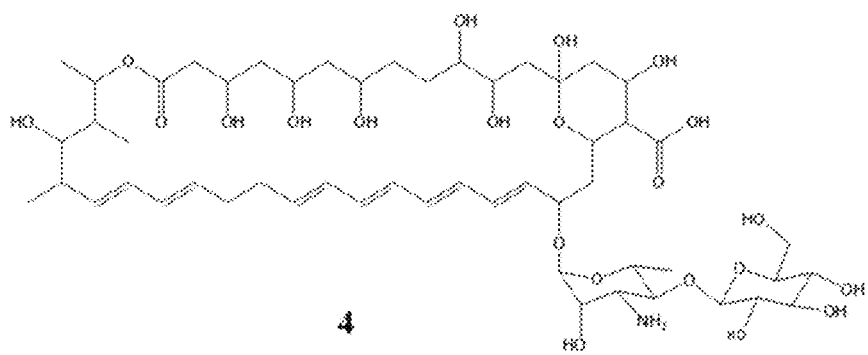
4

POLYENE-SPECIFIC GLYCOSYLTRANSFERASE DERIVED FROM PSEUDONOCARDIA AUTOTROPHICA

CROSS REFERENCE TO PRIOR APPLICATIONS

This application is a National Stage application of PCT International Patent Application No. PCT/KR2014/010161 filed on Oct. 28, 2014, under 35 U.S.C. §371, which claims priority to Korean Patent Application No. 10-2013-0130264 filed on Oct. 30, 2013, which are all hereby incorporated by reference in their entirety.

BACKGROUND

The present invention relates to a polyene-specific glycosyltransferase derived from *Pseudonocardia autotrophica*.

Polyene macrolides are a large family of natural products typically produced by soil actinomycetes. Polyene macrolides are usually biosynthesized by modular and large type I polyketide synthases (PKSs), followed by several steps of sequential post-PKS modifications. In the late stages, a cytochrome P450 oxidizes a methyl side chain to form an exocyclic carboxyl group, and a glycosyltransferase (GT) catalyzes addition of mycosamine, a deoxyaminosugar derived from GDP-d-mannose. Especially, glycosyltransferases are an important class of enzyme and are essential for the biosynthesis of glycosylated natural products because they catalyze the attachment of a sugar to an aglycone. These sugars are often essential for the pharmacological properties, including water solubility and/or the biological activity, of the compounds. Several complementary strategies, including semisynthesis, pathway engineering, and in vitro enzymatic glycosylation techniques, have emerged from recent studies as effective means of altering the natural product sugar structures.

The biosynthetic gene clusters for several polyene macrolides have been characterized. Most polyene antibiotics contain a single deoxyaminosugar attached to the macrolactones. Chemical modification studies have shown that adding sugar residues to polyenes can improve their pharmacological properties. Some polyenes naturally contain additional sugar residues attached to mycosamine. 67-121C, a disaccharide-modified aromatic heptaene, has been isolated from *Actinoplanes caeruleus*. The second sugar residue has been identified as GDP-d-mannose. It was dentified that the extending glycosyltransferase gene, pegA, catalyzed addition of a mannosyl residue to the mycosaminyl sugar during 67-121C biosynthesis. Another example, nystatin P1 with a disaccharide mycosamine-glucose was proposed by MS-MS analysis and a biosynthetic gene cluster identified in the *Pseudonocardia* P1 strain collected from *Apterostigmaden tigerum* garden worker ants. The second sugar residue has not been fully identified but is thought to be a hexose. The gene for the extending GT has been identified and was named nypY.

Most recently, the present inventors identified nystatin-like polyene (NPP) containing a disaccharide, mycosamine (α1-4)-N-acetyl-2-aminoglucose. Interestingly, NPP harboring a disaccharide moiety had more than 300-fold higher solubility and 10-fold lower hemolytic activity than nystatin, which contains only mycosamine. The additional N-acetylglucosamine increased the solubility of the polyene compound. However, the gene for this extending GT was not found in the main biosynthetic gene cluster.

Meanwhile, Korean patent publication No. 10-2010-0089370 discloses biosynthetic gene clusters for polyene derived from *Pseudonocardia autotrophica* and base sequence thereof, however does not mention a novel polyene-specific glycosyltransferase according to the present invention.

Accordingly, the present inventors identified the extending GT in NPP biosynthesis by draft genome sequencing and PCR-targeted gene disruption-complementation system then assessed the function of the coding gene in different polyene-producing strains.

SUMMARY

An object of the present invention is to provide a glycosyltransferase comprising amino acid sequence of SEQ ID NO: 1 and a gene encoding the glycosyltransferase.

Another object of the present invention is to provide a recombinant expression vector comprising the gene and a recombinant microorganism transformed with the recombinant expression vector.

The third object of the present invention is to provide a method of producing a glycosyltransferase comprising: culturing the transformed recombinant microorganism; and isolating a glycosyltransferase from the cultured recombinant microorganism.

To achieve the object of the present invention, the present invention provides provide a glycosyltransferase comprising amino acid sequence of SEQ ID NO: 1 and functional equivalents thereof.

More specifically, the glycosyltransferase is derived from *Pseudonocardia autotrophica* and the glycosyltransferase is polyene-specific.

More specifically, the polyene is nystatin-like polyene (NPP) which is represented by the following Chemical Formula 1:

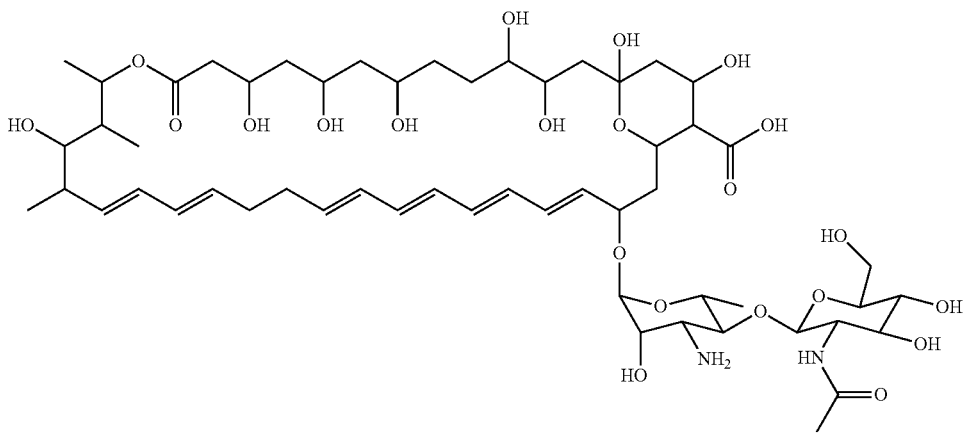

⟨Chemical Formula 1⟩

In addition, the present invention provides a gene encoding the glycosyltransferase.

Preferably, the gene is represented by SEQ ID NO: 2, but is not limited to and may be nucleotide sequences equivalent to the sequence.

Furthermore, the present invention provides a recombinant expression vector comprising the gene and a recombinant microorganism transformed with the recombinant expression vector.

In addition, the present invention provides a method of producing a glycosyltransferase comprising: culturing the transformed recombinant microorganism; and isolating a glycosyltransferase from the cultured recombinant microorganism.

The present invention relates to a novel glycosyltransferase which is derived from *Pseudonocardia autotrophica* and is polyene-specific. According to the glycosyltransferase, nystatin-like polyene (NPP) harboring a disaccharide moiety had higher solubility and lower hemolytic activity than nystatin which contains only a saccharide.

BRIEF DESCRIPTION OF THE DRAWINGS

FIG. 3 illustrates HPLC analysis of NPP and its analogues production in *P. autotrophica* wild type (A), *P. autotrophica*ΔnppY(B), *P. autotrophica*ΔnppY/pnppY(C), *P. autotrophica*ΔnppY/pIJ10257 (D).

FIG. 4 illustrates structure of NPP-related products. Structure of NPP, 1; structure of nystatin A1, 2; structure of 10-deoxynystatin, 3; structure of hexosyl-NPP, 4.

DETAILED DESCRIPTION

Figure 1A:
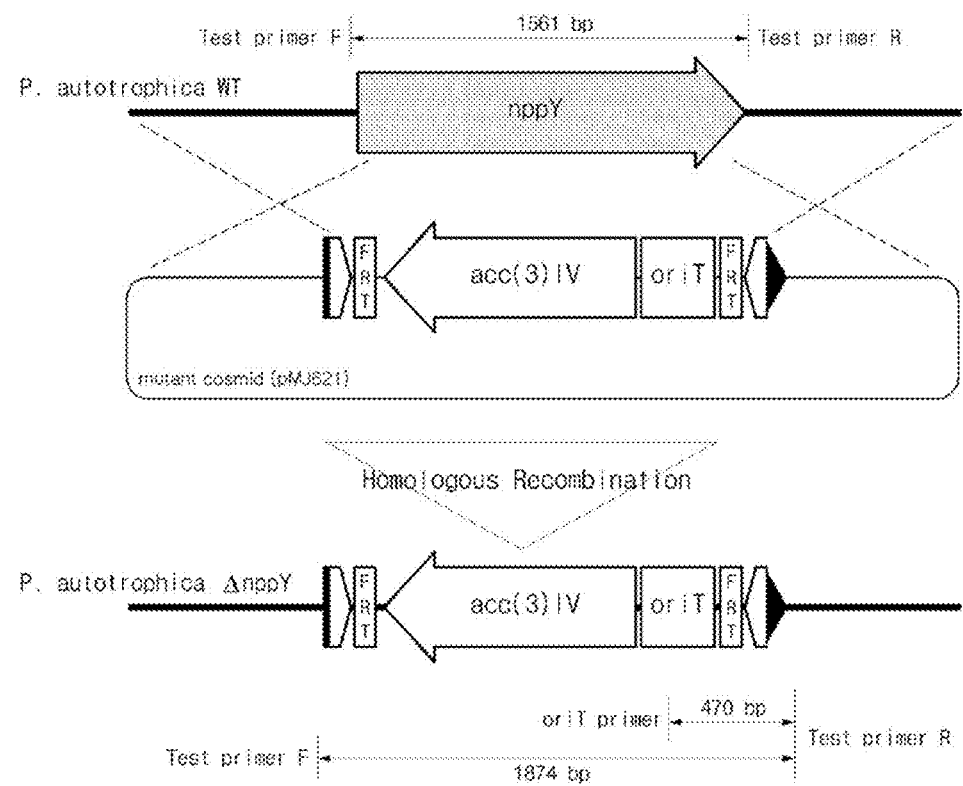
FIG. 1A illustrates a schematic representation of PCR-targeted nppY replacement disruption, and FIG. 1B confirms the constructed *P. autotrophica*ΔnppY mutants by PCR analysis. The expected size of PCR product from wild type (lane 1) and ΔnppY mutant strains (lanes 2 and 3) using check F and check R is 1.5 kb and 1.8 kb and ΔnppY mutant strains (lanes 5 and 6) is about 500 bp using oriT primer-test primer R. DNA size marker in the left end lane is 1 kb labor DNA ladder (lane M1) and 100 bp DNA ladder (lane M2) from Cosmo Genetech, Korea.

The present invention provides a glycosyltransferase comprising amino acid sequence of SEQ ID NO: 1 and functional equivalents thereof.

Specifically, the glycosyltransferase is derived from *Pseudonocardia autotrophica* and the glycosyltransferase is polyene-specific. More specifically, the polyene is nystatin-like polyene (NPP) which is represented by the following Chemical Formula 1:

⟨Chemical Formula 1⟩

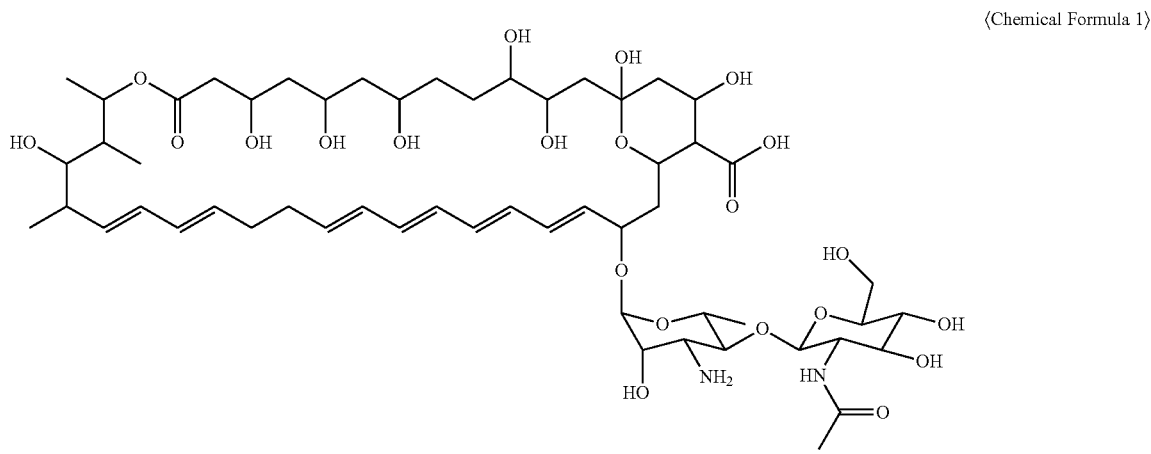 [SMILES: CC(=O)NC1C(OC2C(C)OC(OC3/C=C/C=C/C=C/C=C/CC/C=C/C=C/C(C)C(O)C(C)C(C)OC(=O)CC(O)CC(O)CC(O)CCC(O)C(O)CC4(O)CC(O)C(C(=O)O)C(C3)O4)C(O)C2N)OC(CO)C(O)C1O]

The term "functional equivalent" includes amino acid sequence variants having substitutions in some or all of the amino acids of SEQ ID NO. 1, or deletions or additions in some of the amino acids, and refers to those having physiological activity substantially equivalent to thereof. Substitutions of the amino acids are preferably conservative substitutions. Examples of conservative substitutions of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). Deletion of the amino acids is preferably located at regions that are not directly involved in the physiological activity of the glycosyltransferase.

In addition, the present provides a gene encoding the glycosyltransferase. Preferably the gene is represented by SEQ. ID. 2 and is not limited to, and provides nucleotide sequences equivalent to the sequence.

As used herein, "nucleotide sequences equivalent" include the codon degenerate sequence of the anticancer peptide. As used herein, the term "codon degenerate sequence" means a nucleotide sequence which differs from the sequence, but encodes a polypeptide having the same sequence as that of the glycosyltransferase disclosed in the present invention.

In addition, the present invention provides a recombinant vector comprising the gene and a recombinant microorganism transformed with the recombinant expression vector.

In addition, as used herein, the term "vector" means a DNA molecule which is self-replicated and used to carry the gene done (or any other fragment of clone DNA).

As used herein, the term "expression vector" means a recombinant DNA molecule comprising a desired coding sequence and appropriate nucleic acid sequences are essential to express the coding sequence operably linked to in a specific host organism. Expression vectors will preferably include at least one selectable marker. The marker is typically a nucleic acid sequence which has the properties that can be selected in a chemical way, all the genes which can be distinguished from non-transformed cells, the transformed cells are the equivalent characteristics. Examples are antibiotic resistance gene such as ampicillin, kanamycin, G418, bleomycin, hygromycin, chloramphenicol, but are not limited to and can be appropriately selected by those skilled in the art.

Furthermore, the present invention provides a method of producing a glycosyltransferase comprising: culturing the transformed recombinant microorganism; and isolating a glycosyltransferase from the cultured recombinant microorganism.

Details associated with genetic engineering techniques used in the present invention can refer to reference including Sambrook, et al. (Molecular Cloning, A Laboratory Manual, Cold Spring Harbor laboratory Press, Cold Spring Harbor, N.Y. (2001)) and Frederick et al. (Frederick M. Ausubel et al., Current protocols in molecular biology volume 1, 2, 3, John Wiley & Sons, Inc. (1994)).

The present invention will be described more fully hereinafter with reference to the accompanying drawings, in which exemplary embodiments of the invention are shown.

Example 1 Pseudonocardia autotrophica Genome Sequencing and Bioinformatics of GTome 1. Bacterial Strains, Culture Conditions, and DNA Manipulation Escherichia coli DH5α was used as a cloning host. Plasmids were propagated in E. coli ET12567 (dam2, dcm2, hrdM) to obtain unmethylated DNA for transformation into P. autotrophica. E. coli was grown in Luria-Bertani (LB) broth and maintained on LB agar medium at 37° C., supplemented with the appropriate antibiotics when needed. P. autotrophica (KCTC 9441) obtained from Korean Collection for Type Cultures (KCTC, Korea) was grown routinely in ISP medium 2 (glucose 0.4%, yeast extract 0.4%, malt extract 1%, agar 2%) at 30° C. for sporulation. P. autotrophica spores were re-suspended and stored in a sterile 20% glycerol solution at −20° C. For total DNA isolation, spore suspensions were inoculated into 25 ml of YEME liquid media, and cultured for 2 days at 30° C. Isolation of the DNA fragments from E. coli and agarose gel was conducted using a LaboPassKit (Cosmo Genetech, Korea). Oligonucleotide primers were purchased from Cosmo Genetech.

2. P. autotrophica Genome Sequencing for Identification of GTome

The draft genome sequence of S. benihana was obtained on the 454 GS-FLX (Roche) system and by traditional shotgun whole-genome Sanger sequencing, resulting in two genome libraries (insert size ~2 kb and ~35 kb) generated by random shearing of genomic DNA. The sequence data were assembled using the Newbler, Phred/Phrap/Consed package and in-house scripts. Protein-coding genes and their functions were predicted as described previously.

3. Results

The draft genome sequence of P. autotrophica comprised 9,977,725 bases, assembled into 1,016 contigs (>500 bp), and it had a GC content of 69.9%. Further, there were 96 predicted tRNAs sequences along with 10,581 protein-coding sequences (CDSs) in the genome sequence. Specifically, the coding percentage was 70.5%, and 7,466 CDSs showed functional predictions. Using COG functional assignment, the majority of predicted proteins were classified into 25 COG categories. We identified about 100 glycosyltransferase (GT) genes from P. autotrophica and efforts to obtain complete sequence are in progress.

One 32,228 bp contig was found to contain a part of known NPP gene cluster from nppF to nppI, one metallophosphoesterase homologous gene and two additional glycosyltransferase genes as well. The order of genes was identical to that in the nystatin P1 biosynthetic gene cluster. The additional genes were named nppZ (metallophosphoesterase), nppX and nppY (glycosyltransferases). Interestingly, nppY is located immediately upstream of the nppF gene like nypY in Pseudonocardia P1. The NppY protein displays 82% amino acid identity to NypY, which adds a hexose to the mycosamine of a nystatin polyene and 51% identity to PegA, which is the extending glycosyltransferase that adds the second sugar of 67-121C, but only 42% to NppDI. The other glycosyltransferase in the same contig, NppX shows about 30% amino acid identity with 1L-myo-inositol-1-phosphate-1-alpha-D-N-acetylglucosaminyl-transferase from Rhodococcus sp. Therefore NppY is the most likely candidate for NPP extending glycosyltransferase, which catalyzes addition of a glucosamine residue to the mycosaminyl sugar unlikely to be a functionally redundant copy of NppDI during NPP biosynthesis.

Example 2 Identification and Characterization of nppY Gene in P. autotrophica

1. Construction of nppY-Disrupted Mutant P. autotrophica ΔnppY

The P. autotrophica mutant strain was constructed using the PCR-targeted gene disruption system. An apramycin-resistance gene/oriT cassette for the replacement of the nppY gene was amplified using pIJ773 as a template and the following primers: forward primer (5-ttttcccggcccccgcggtg-gtgcactggccgcatggagATTCCGGGGATCCGTCGACC-3') and reverse primer (5-gtcgaactggtcgacgaggtgggacggaccag-cacgggaacTGTAGGCTGGAGCTGCTTC-3'). The lower-case type represents 40 nt homologous extensions to the DNA regions inside the nppY gene. The resultant PCR product was used to target the cosmidpESK621 containing the nppY gene in E. coli BW25113/pIJ790. The mutated cosmid was transferred to P. autotrophica by conjugation via ET12567/pUZ8002, and the desired mutants, which were the products of double crossovers, were identified by screening for colonies that were apramycin resistant but kanamycin sensitive. The double-crossover exconjugants were selected using the standard $apr^R/kan^S$ method, followed by confirmation of both P. autotrophica and P. autotrophicaΔnppY genomic DNAs by PCR. Three different PCR primers used to confirm the double cross-over recombinants were nppY test primer F (5'-CGGGATCCCG ACCGGGGCCTGCTCGTCA-3'), nppY test primer R (5'-GCTCTAGAGC CGGGTGGTCCCGCTGGTGG-3') and oriT test primer F (5'-gaattcagcgtgacatcattctgtgg-3'), which is in the aprR/oriT cassette.

2. Complementation of nppY Gene-Disrupted P. autotrophica Mutant

A1561 bp fragment encompassing the nppY coding sequence was PCR amplified from P. autotrophica genomic DNA with same oligonucleotides for test of nppY gene disruption. The PCR product was excised from the resulting construct as BamHI/XbaI fragment, and ligated into the sites of the integrative vector pMMBL005, yielding plasmid pnppY. The plasmid harboring nypY gene, pIJ10257 which was kindly provided by Prof. Hutchings (UK), was also used for nppY complementation. The resulting recombinant plasmids were introduced into the P. autotrophicaΔnppY mutant strain individually.

3. HPLC Quantification for NPP Production

P. autotrophica strains were cultivated at 28° C. YEME agar media for 3 days for NPP production. Extracts were prepared by extraction with an equal volume of buthanol, followed by concentration and methanol resuspension. A Shimadzu SPD M10A (Shimadzu, Japan) with a ZORBAX RX-C18 column (5 μm, 4.6×150 mm, Agilent) was used for the assay. The sample injection volume was 20 μl and the run time was fixed at 35 min. The column was equilibrated with 50% solvent A (50 mM ammonium acetate pH 6.5) and 50% solvent B (Methanol), and developed using the following gradient: 50% B (0 min), 90% B (21 min), 100% B (25 to 30 min), 50% B (33 to 35 min) at a flow rate of 1 ml/min and UV/vis detection at 305 nm. The mass spectrometer was run in positive ion detection mode and set to scan between 100 and 1500 m/z.

4. Results

Figure 1B:
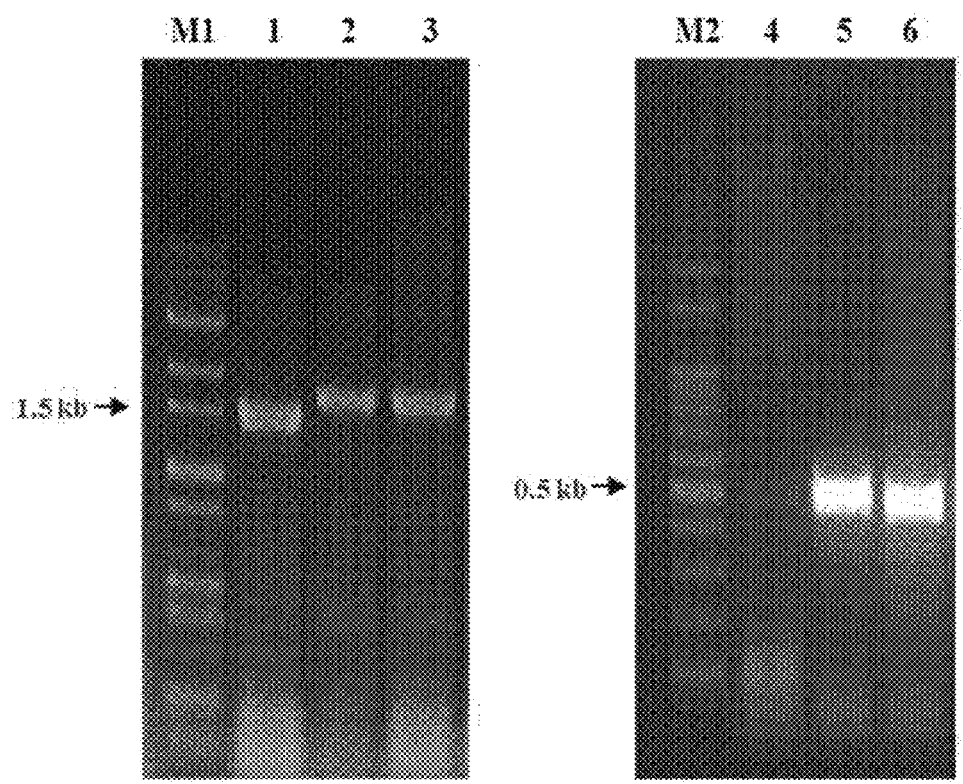

To verify the function of putative NPP extending glycosyltransferases, inactivation of the nppY was performed by the *Streptomyces* PCR-targeted gene disruption system. A 1473 bp-nppY gene in cosmid pESK621 was replaced with an apramycin resistance/oriT cassette, generating mutant cosmidpMJ621, which was introduced into *P. autotrophica* by conjugative gene transfer (FIG. 1A). Construction of the nppY-deleted mutant (named *P. autotrophica*ΔnppY) was confirmed by PCR analysis. The expected 1.5 kb PCR-amplified band was observed in genomic DNA samples isolated from *P. autotrophica*, and a band at the expected size (1.8 kb) was observed in genomic DNA samples isolated from *P. autotrophica*ΔnppY (FIG. 1B). Moreover a PCR-amplified fragment with the expected size (0.47 kb), amplified using an alternative PCR primer pair designed to detect theapramycin resistance gene/oriT cassette, was observed only in the *P. autotrophica*ΔnppY strain, indicating that the nppY gene in *P. autotrophica* was specifically disrupted as expected (FIG. 1B).

*P. autotrophica* wild-type and three independently-isolated *P. autotrophica*ΔnppY mutant strains were cultured and optimized for polyene production, followed by HPLC-MS analysis (FIGS. 3A and 3B). The major products present were compound 3 along with some of 2, and their structures were estimated via MS analysis. The MS spectrum of 3 contained a signal at m/z 909 (calculated mass). Using this analysis, the mass of this compound was shown to be smaller than compound 1, consistent with deoxynystatin, indicating that the compound 3 accumulated in nppY-disrupted mutant lacked both the C-10 hydroxyl and the second sugar moieties (FIG. 4). This analysis revealed that not only the second sugar but the oxygen atom was not present in 3, and thus NppL might not be able to hydroxylate not only deoxyNPP but deoxynystatin at the C-10 position. Despite of the high degree of sequence homology between NysL and NppL (68% identity), the latter enzyme only weakly recognizes deoxynystatin as substrate.

Figure 2A:
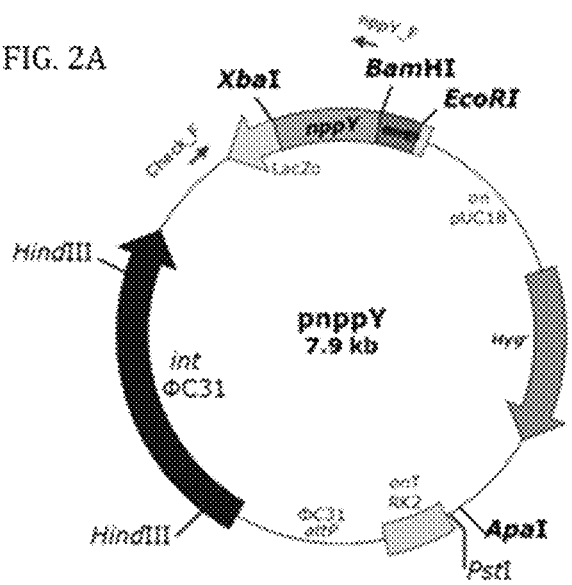
FIG. 2A shows a map of nppY genes in the *Streptomyces* expression vector, pMMBL005 (pnppY)
Figure 2B:
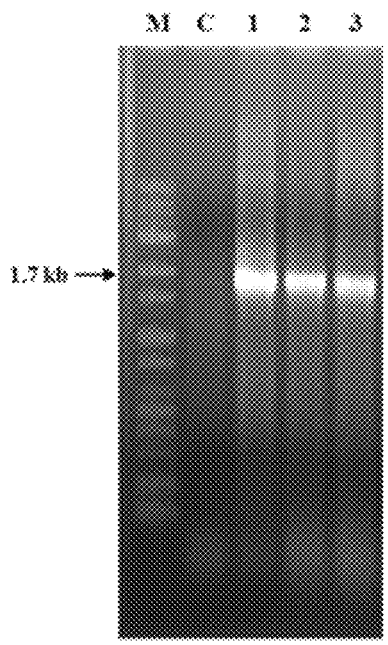
FIG. 2B shows PCR with the genomic DNA samples. Lane M, 1 kb DNA ladder; lane C, wild type; lane 1, pnppY plasmid; lane 3, *P. autotrophica*ΔnppY/pnppY.

To confirm that NppY is indeed responsible for additional glycosylation of nystatin, we performed trans-complementation of *P. autotrophica*ΔnppY mutant by expressing nppY under the control of the ermE*p promoter. For these experiments, we used the integrating conjugative vector pMMBL005, into which the coding region of nppY was cloned, resulting in pnppY (FIG. 2A). The plasmid was introduced into *P. autotrophica*ΔnppY by conjugation, and the resulting *P. autotrophica*ΔnppY/pnppY strain was confirmed by PCR analysis (FIG. 2B). HPLC-MS analysis demonstrated that NPP production was restored in *P. autotrophica*ΔnppY/pnppY strain (FIG. 3C), indicating that the absence of NPP from *P. autotrophica*ΔnppY was due to a lack of the nppY gene. These results indicate that NppY is the extending glycosyltransferase that adds the second sugar of NPP.

The function of nppY gene was investigated by heterologous expression in other mycosaminyl-polyene producer *S. noursei* and *S. nodosus* strains. The pnppY construct was introduced those strains by conjugation and the recombinant strains (named as *S. noursei*/pnppY and *S. nodosus*/pnppY) were confirmed by PCR analysis (FIG. 5), followed extraction and HPLC analysis. The main products were nystatin for *S. noursei*/pnppY and amphotericins A and B for *S. nodosus*/pnppY. No extra polyene species were detected as convincing peaks in the chromatograms. Expression of the gene in other polyene producers does not lead to the production of disaccharide-modified nystatin or amphotericins.

Figure 2C:
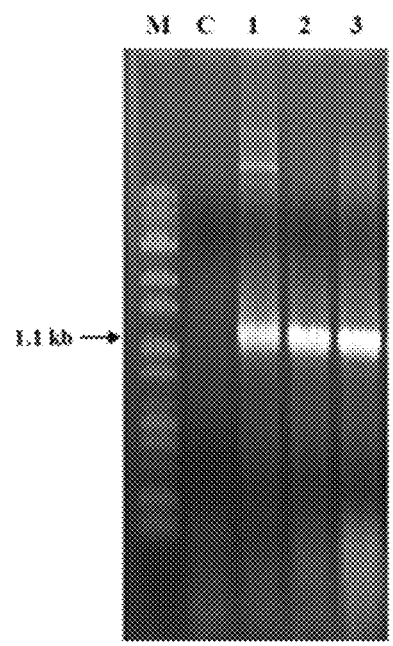
FIG. 2C shows PCR with the genomic DNA samples. Lane M, 1 kb DNA ladder; lane C, wild type; lane 1, pIJ10257 (pnypY) plasmid; lane 3, *P. autotrophica*ΔnppY/pIJ10257.

Further characterization of the nppY gene product via database-assisted in silico analysis revealed that it encodes a 490 aa-containing protein, showing 82% amino acid identities to polyene extending glycosyltransferase NypY from *Pseudonocardia* P1. The *P. autotrophica*ΔnppY mutant was complemented with the nypY cloned under the control of the ermE*p promoter, plasmid pIJ10257 which kindly provided by Prof. Hutchings. The plasmid was introduced into the *P. autotrophica*ΔnppY mutant strain resulting *P. autotrophica*ΔnppY/pnypY and confirmed by PCR analysis (FIG. 2C).

The invention claimed is:

1. A recombinant expression vector comprising a gene nppY encoding a glycosyltransferase comprising the amino acid sequence of SEQ ID NO: 1, wherein the glycosyltransferase is obtained from *Pseudonocardia autotrophica*, wherein the gene comprises the sequence of SEQ ID NO: 2.

2. A recombinant microorganism transformed with the recombinant expression vector of claim 1.

3. A method of producing a glycosyltransferase comprising:

culturing the transformed recombinant microorganism of claim 2; and isolating the glycosyltransferase from the cultured recombinant microorganism.

* * * * *

SEQUENCE LISTING

<160> NUMBER OF SEQ ID NOS: 2

<210> SEQ ID NO 1
<211> LENGTH: 475
<212> TYPE: PRT
<213> ORGANISM: Pseudonocardia autotrophica

<400> SEQUENCE: 1

Met Glu Gln Thr Thr Gly Thr Gln Arg Ala Asp Gly Pro Gly Gln Glu
1               5                   10                  15

Ala Asp Gln Ala Gly Ala Arg Pro Val Leu Phe Cys Cys Thr His Ser
            20                  25                  30

Thr Gly Glu Ala Ala Thr Ser Leu Ala Leu Ala Gly Glu Leu Ala Arg
        35                  40                  45

Arg Gly Val Pro Asp Leu Val Phe Ala Ala Asp Glu Asn Leu Arg Gly
    50                  55                  60

Pro Val Glu Glu Ile Ala Asp Arg Ser Ala Val Glu Phe Val Ser Leu
65                  70                  75                  80

Gly Pro Val Asn Pro Ala Leu Ala Leu Thr Met Met Asp Asp Ala Thr
                85                  90                  95

```
Tyr Asp Arg Ile Tyr Gln Arg Ser Arg Val Arg Ala Leu Arg Ala Arg
                100                 105                 110

Ala Arg Gln Leu Phe Asp Val Asp His Leu Leu Gln Arg Tyr Gln Ala
            115                 120                 125

Leu Asp Glu Val Val Glu Arg Val Arg Pro Ala Leu Met Val Ile Asn
130                 135                 140

Arg Phe Ala Thr His Ala Val Leu Val Ala Leu Ala Arg Asp Ile Pro
145                 150                 155                 160

Tyr Val Ile Thr Ala Pro Cys Leu Leu Ser Ser Leu Val Glu His Asp
                165                 170                 175

Leu Pro Arg Gly Phe Pro Pro Ser Ser Gly Leu Pro Leu Arg Arg
            180                 185                 190

Thr Leu Arg Gln Glu Leu Asp Arg Ile Trp Phe Arg Ile Gly Val Gly
            195                 200                 205

Ser Leu Phe Leu Asp Arg Ser Val Leu Arg Arg Ala Val Arg Leu His
            210                 215                 220

Lys Arg Met Gly Glu Leu Gly Leu Asp Pro Arg Thr Leu Arg Ala Pro
225                 230                 235                 240

Val Gln Gln Glu Gly Ala Arg Ser Leu Leu Cys Phe Thr Val Pro Gly
                245                 250                 255

Val Asp Tyr Pro Leu Pro Val Pro Asp Arg Val Arg Met Val Gly Ala
            260                 265                 270

Leu Val Pro Pro Ser Arg His Asp Glu Arg Asp Ala Ala Val Thr Glu
            275                 280                 285

Trp Leu Asp Ala His Pro Ser Val Val Tyr Val Ala Phe Gly Ser Val
            290                 295                 300

Thr Arg Met Thr Ala Asp Gln Val Arg Ser Leu Val Glu Leu Ala Arg
305                 310                 315                 320

Arg Leu Gly Asp Asp His Gly Leu Leu Trp Val Leu His Arg Asp Gln
                325                 330                 335

Gln Arg Leu Leu Pro Ala Glu Leu Pro Ala Asn Leu Lys Val Val Pro
            340                 345                 350

Trp Val His Ser Gln Leu Gly Val Leu Glu His Pro His Val Arg Ala
            355                 360                 365

Phe Phe Thr His Gly Gly Ser Asn Ser Ile His Glu Ser Leu Tyr Phe
            370                 375                 380

Gly Val Pro Val Leu Val Arg Pro Thr Leu Val Asp Gln Phe Asp His
385                 390                 395                 400

Ala Val Arg Ala Val Asp Thr Gly Ile Gly Leu Thr Val Glu Arg Pro
                405                 410                 415

Asp Arg Ile Asp Val Asp Asp Thr His Gly Arg Leu Leu Arg Leu Leu
            420                 425                 430

His Glu Pro Gly Phe Ala Asp Arg Ala Arg Glu Ile Gly Gln Val Gln
            435                 440                 445

Arg Ser Ala Gly Gly Leu Arg Val Ala Gly Asp Ala Val Leu Met Glu
            450                 455                 460

Leu Arg Glu Ala Ser Val Pro Thr Pro Ser Ala
465                 470                 475

<210> SEQ ID NO 2
<211> LENGTH: 1428
<212> TYPE: DNA
<213> ORGANISM: Pseudonocardia autotrophica
```

```
<400> SEQUENCE: 2
atggagcaga ccaccggcac gcagcgggcc gacggccccg dacaggaggc ggatcaggcc    60
ggtgcgcggc cggtcctgtt ctgctgtacc cactccaccg gggaggccgc caccagtctc   120
gcgctcgccg gcgagctggc ccggcgcggc gtaccggacc tcgtgttcgc cgccgacgag   180
aacctccgcg gcccggtcga ggagatcgcc gaccgcagcg cggtggagtt cgtctccctg   240
ggcccggtga accggcgct ggcactcacc atgatggacg acgcgaccta tgaccggatc   300
taccagcggt cccgggtccg cgcgttgcgc gcacgggccc ggcagctgtt cgacgtcgac   360
cacctgctgc agcgctacca ggccctcgac gaggtcgtcg agcgtgtccg ccccgccctg   420
atggtgatca accggttcgc cacgcacgcc gtcctggtcg cgctggcccg cgatatcccc   480
tacgtcatca ccgcaccgtg cctgctcagc agcctcgtcg agcacgacct gccgcgcggg   540
ttccccccgc cgtcgtccgg gctgccgctg cgccgcaccc tgcgccagga gctggaccgg   600
atctggttcc ggatcggcgt gggcagcctg ttcctcgacc gttcggtgct gcgcagggcc   660
gtccggctgc acaagcggat gggcgagctc gggctcgacc cgcgcacgct gcgcgccccg   720
gtccagcagg agggcgcccg ctccctgctc tgcttcaccg tccccggggt cgactacccg   780
ctaccggtcc cggaccgggt acggatggtg ggggcgctcg tcccccccgag ccgccacgac   840 gagcgcgacg cggccgtcac cgagtggctc gacgcgcacc cgtcggtcgt ctacgtggcg   900
ttcggctcgg tgacccggat gacggccgat caggtccggt cactcgtcga gctggcccgc   960
aggctcggcg acgaccacgg cctgctctgg gtgctgcacc gggaccagca gcgtctcctg  1020
cccgccgagc tgccggcgaa cctgaaggtg gtgccctggg tccattccca gctcggggtc  1080
ctggagcacc cgcacgtccg ggcgttcttc acccacgggg ggagcaacag catccacgag  1140
agcctctact tcggggttcc cgtgctggtc cgtcccaccc tcgtcgacca gttcgaccac  1200
gcggtccgtg cggtcgacac ggggatcggg ttgaccgtcg agcggccgga ccgcatcgac  1260
gtcgacgaca cccacggcag gctgctgcgg ttgctgcacg aacccgggtt cgccgaccgc  1320
gcgcgggaga tcgggcaggt ccagcgatcc gccggcgggc tccgcgtggc cggtgacgcc  1380
gtgctgatgg agcttcgcga agcgtcggta ccgacccca gcgcctga                1428
```